United States Patent [19]
Michael

[11] Patent Number: 5,306,145
[45] Date of Patent: Apr. 26, 1994

[54] DENTAL MODEL PREPARATION AND APPARATUS THEREFOR

[76] Inventor: Robert M. Michael, 116 N. Road, Rte. 5, Johnson City, Tenn. 37601

[21] Appl. No.: 80,188

[22] Filed: Jun. 24, 1993

Related U.S. Application Data

[63] Continuation of Ser. No. 821,179, Jan. 15, 1992, abandoned.

[51] Int. Cl.5 .............................................. A61C 19/00
[52] U.S. Cl. ...................................................... 433/34
[58] Field of Search ............... 433/34, 60, 74; 264/16, 264/17, 18

[56] References Cited

U.S. PATENT DOCUMENTS

| | | | |
|---|---|---|---|
| 3,436,827 | 4/1969 | Dew | 433/34 |
| 3,581,398 | 6/1971 | Thomas | 433/34 |
| 4,439,151 | 3/1984 | Whelan | 433/60 |
| 4,508,506 | 4/1985 | Jackson | 433/74 |
| 4,538,987 | 9/1985 | Weissman | 433/34 X |
| 4,708,648 | 11/1987 | Weissman | 433/34 X |
| 4,721,464 | 1/1988 | Roden et al. | 433/34 X |
| 4,842,242 | 7/1989 | Huffman | 264/17 X |
| 4,957,435 | 9/1990 | Jinoian et al. | 433/34 |
| 5,129,822 | 7/1992 | Dobbs | 433/34 |

*Primary Examiner*—Gene Mancene
*Assistant Examiner*—Nicholas D. Lucchesi

[57] ABSTRACT

A dental stone casting mold adapted to a single casting process for the preparation of a positive tooth replica, the mold having opposed side walls, end walls and a floor forming a cavity for containing fluid or set dental stone, a pair of cooperating interlocking mechanisms, one of the mechanisms being carried by the mold floor and the other being adapted for fixation to the dental stone, each mechanism being cooperatively configured with respect to the other such that when they are forced toward a mating position, vector forces are created tending to urge the set dental stone toward the mold floor.

11 Claims, 3 Drawing Sheets

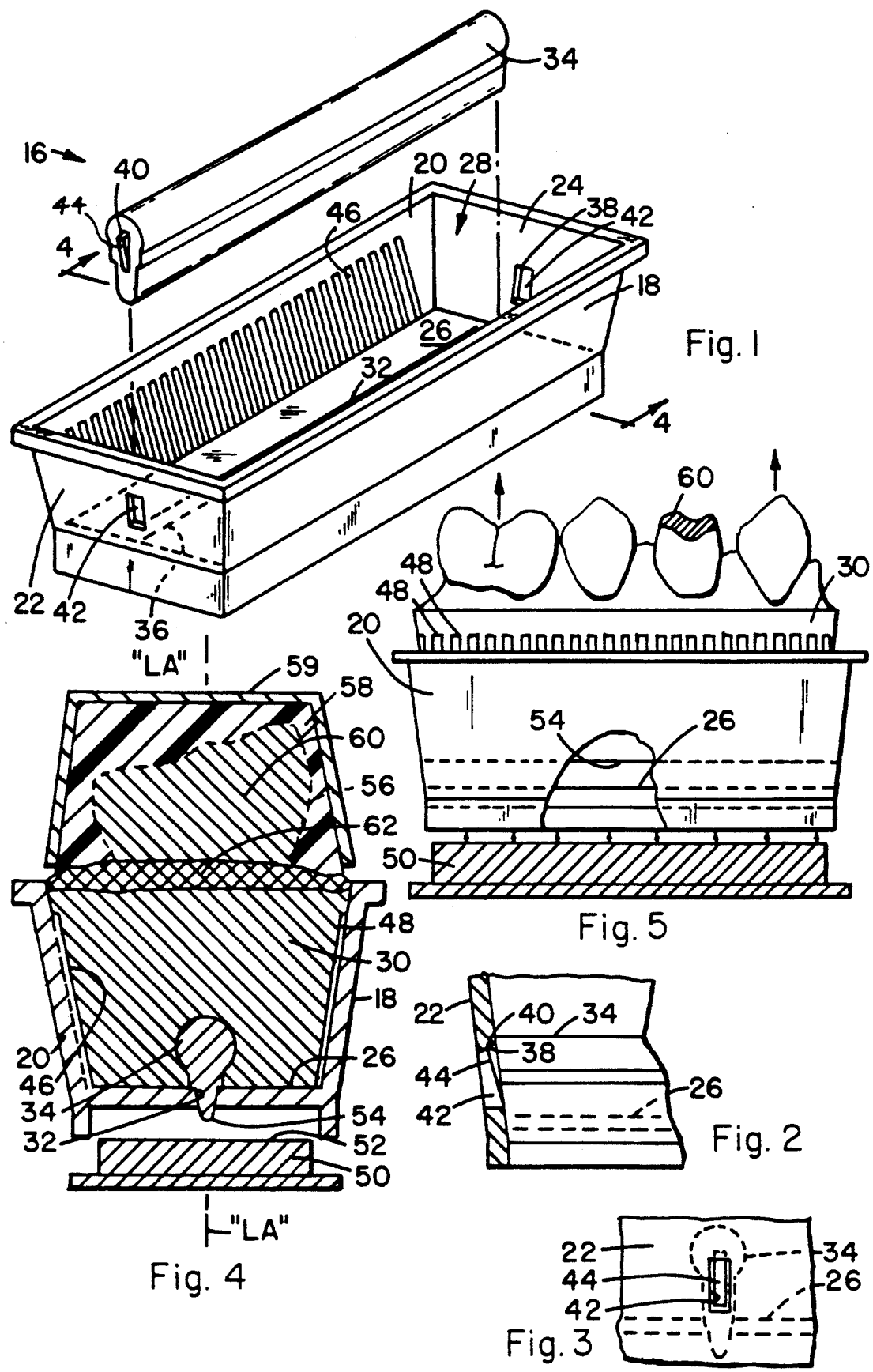

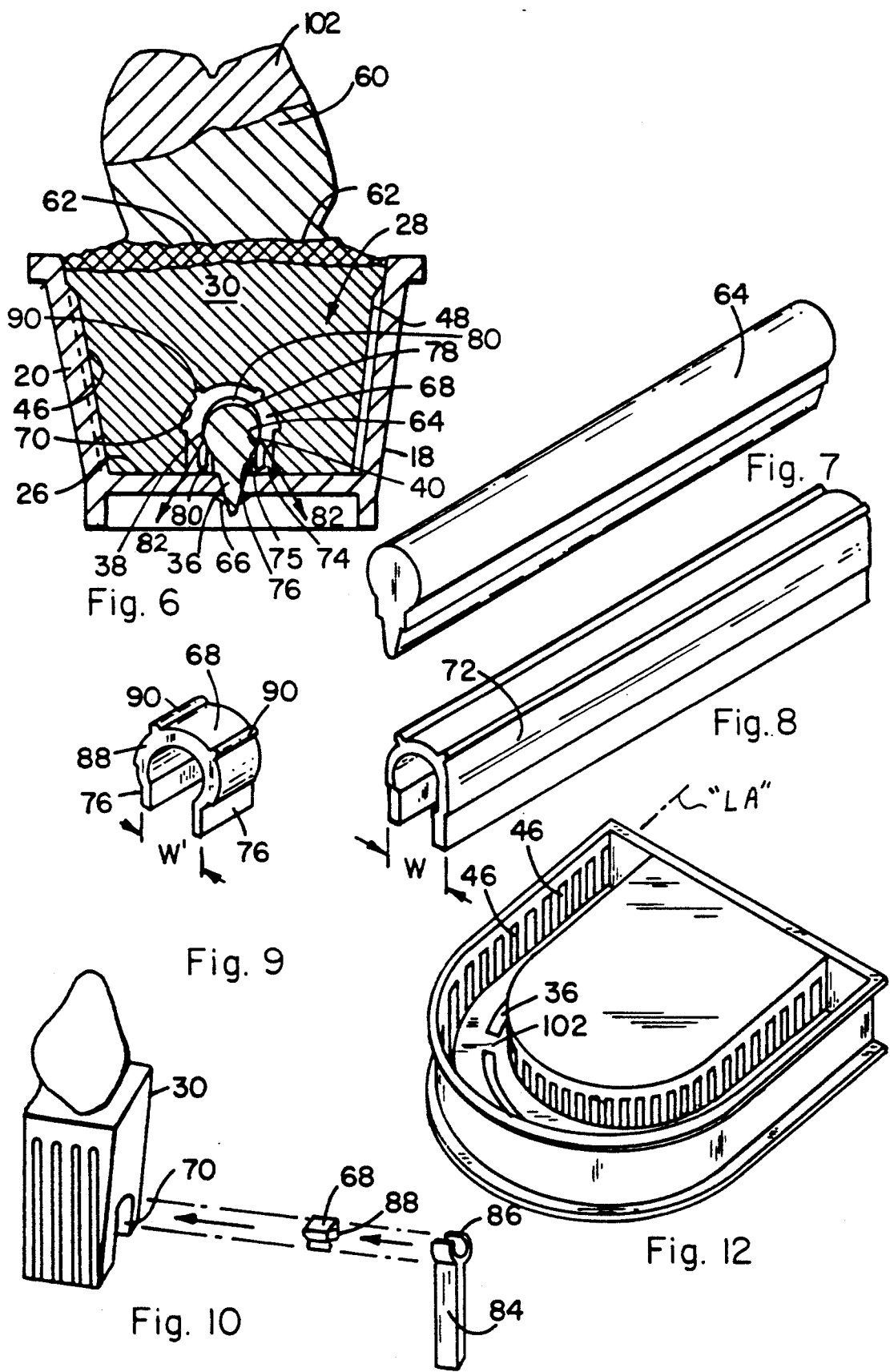

DENTAL MODEL PREPARATION AND APPARATUS THEREFOR

This application is a continuation of Ser. No. 07/821,179, now abandoned.

FIELD OF INVENTION

The present invention relates to a method for the preparation of dental models and to special apparatus for carrying out the method, more particularly, to the provision of novel retention and positioning means for removably locating and securing model teeth in dental stone casting molds or trays.

BACKGROUND OF INVENTION

In the field of dental care, replacement teeth are typically retained in place by means of bridge work or the like extending from the replacement tooth and anchored to adjacent healthy teeth. The manufacture of such replacement teeth and their mechanical bridge structure requires careful work to insure proper fitting thereof with respect to adjacent teeth. Also, restoration procedures such as the capping of decayed or broken teeth likewise requires close attention to the precise positions of proximate teeth.

To accurately form and position the replacement tooth or cap, a dentist usually makes a dental negative or impression of the relevant tooth or gap, typically including at least the adjacent teeth. This impression may be partial, unilateral or bilateral, depending upon the extent of the work to be done, and serves as a mold for eventually developing, e.g., a die of the patient's tooth to be replaced or restored. For example, when a tooth is to be crowned or otherwise rebuilt, it is conventional to make a negative casting or impression of the tooth using a rubber-like impression material, the impression then being used as a mold for preparing a positive replica of the tooth to be restored. The replica is then used to assist in forming a crown model of the tooth which, in turn, provides a form or die for making the crown. If needed, a full-bite positive replica of the teeth will be prepared for use in ensuring that the upper and lower teeth sets will close together properly.

DISCUSSION OF PRIOR ART

During preparation of the replica tooth or cap, it is usually necessary to remove the casting of its precursor or mock-up from the complete casting, often several times. To do this the casting, e.g., a jaw-shaped positive or replica of the gum and upper or lower teeth set, is cut through and a slice of replica gum and teeth set removed from the set. In this regard, in order to provide a template on which to reassemble the pieces of the set, a removable base is typically affixed, e.g., by casting onto the replica teeth set and gum before it is cut up. In order that the individual pieces may be accurately reassembled in the initial mold, and in accordance with prior art practises each piece is provided with a locating pin or the like which fits into a hole in the base. The pins are set into the replica pieces during the molding operation.

This technique for preparing the replica such that it can be reassembled in a mold or on a base in proper relation to the adjacent teeth in the set requires that the pins be very accurately positioned in the fluid dental stone from which the replica tooth or teeth are to be formed. This procedure is difficult since, e.g., the mold is filled with molding material thus obscuring the pins, and also the outline of the teeth is not visible from the outside of the mold. Such drawbacks to prior procedures, including the need for multi-casting steps and the like are either evident from or are discussed in detail in U.S. Pat. Nos.: 4,122,606; 4,398,884; 4,368,042; 4,078,310; 4,943,237; 4,767,330; 4,265,619; 4,299,574; 3,937,773; 4,917,347; 4,403,961; 4,854,875; the disclosures of which are incorporated herein by reference.

OBJECTS OF THE INVENTION

Objects of the present invention therefore are: to provide a method and apparatus for the preparation of positive dental castings which requires only a single dental stone casting step in a greatly simplified casting mold device or tray; to provide such a mold device which can be used repeatedly for different castings and for repeated reinsertions or reassemblies of previous casting sections therein for proper prosthesis build-up or further working; to provide such a device which is readily adapted for use with full-bite articulators; to provide such mold device which itself can be manufactured from a variety of materials in a single plastic or ceramic molding or metal forming manufacturing operation; and to provide such method and apparatus which require minimum labor intensity and minimum expertise for their utilization.

BRIEF SUMMARY OF THE INVENTION

The above and other objects hereinafter appearing have been attained in accordance with the present invention which in its apparatus embodiment is defined as a dental stone casting mold device or tray comprising associated side wall means, end wall means, and floor means forming cavity means for containing fluid or set dental stone material, cooperating interlocking but separable retaining means, one of said retaining means being carried by said device and the other being adapted for fixation to said dental stone material, each said retaining means being cooperatively configured with respect to the other such that in their interlocked position, the set dental stone is firmly held in said device.

In certain preferred embodiments:

(a) said retaining means are configured such that in their interlocked position they generate vector forces tending to urge the set dental stone material toward said floor means;

(b) the configuration of each said retaining means provides a cooperating cam surface means adapted to contact and frictionally slide over the other cam surface means to generate said vector forces;

(c) at least one of said retaining means is resiliently distortionable by contact with the other, and the potential energy of said vector forces is generated by resilient distortion of said at least one retaining means during forcing thereof toward its interlocking position;

(d) the mold device is shaped to provide elongated cavity means, and wherein each said retaining means is elongated and oriented substantially longitudinally of said cavity means;

(e) the mold device is shaped to provide elongated cavity means, and wherein said one retaining means is elongated and removably affixable to said floor means substantially longitudinally of said cavity means;

(f) the mold device as aforesaid wherein each of said cam surface means has a substantially wedge-shaped, cross-sectional configuration, and is oriented with respect to the other in mated condition such as to generate vector forces on said dental stone material directed generally toward said floor means;

(g) the mold device as aforesaid wherein substantially longitudinally extending slot means is provided in said floor means and is adapted to function either as the elongated retaining means thereon, or as a supporting structure for said one elongated retaining means inserted therethrough; and (h) the wall means of said tray are slightly slanted outwardly from bottom to top to provide draft angles for easy removal from and reinsertion therein of the dental casting.

In its procedural aspect, the present invention is defined as the method for preparing a dental stone positive tooth casting comprising providing a casting mold device having interconnected side wall means, end wall means and floor means providing base cavity means adapted for containing fluid or set dental stone material for forming a casting base, providing on said device within said cavity means one component of a separable, interlocking retaining unit, mounting the other component, or its precursor, of said retaining unit in substantially interlocking position on said one component, filling said base cavity means with fluid dental stone, providing dental impression means filled with fluid dental stone, bringing the exposed surfaces of the fluid dental stone of said base cavity means and said dental impression means into fluid contact with each other to form a bonding interface therebetween, and allowing said dental stone material to harden and affix said other component, or its presursor, of said retaining unit thereto for allowing removal from and reinsertion into said base cavity means of the resultant positive tooth casting, said components of said unit being cooperatively configured such that in their interlocked position, the set dental stone is firmly held in said mold device.

In a preferred embodiment of the above method, each said component is cooperatively configured with respect to the other such that when they are forced toward a mating position, vector forces are created tending to urge the set dental stone casting toward said floor means.

BRIEF DESCRIPTION OF THE DRAWINGS

The invention will be further understood from the following drawings, not to scale, and description thereof wherein:

FIG. 1 is an isometric view of an embodiment of a casting mold device or tray, including one embodiment of retaining means in accordance with the present invention;

FIG. 2 is a longitudinal cross-sectional view of a portion of one end of the mold device showing the interlocked retaining means of FIG. 1;

FIG. 3 is an end view of the mold device showing the interlocked retaining means of FIG. 1;

FIG. 4 is a cross-sectional view of the mold device of FIG. 1 containing a positive dental casting of a tooth to be capped, the view being taken along line 4—4 of FIG. 1 with the filled dental impression shown in position for forming said bonding interface;

FIG. 5 is a side view of the mold device of FIG. 4 containing a positive dental casting which has been pushed upwardly out of the mold device, and with the elastomeric impression material removed from the positive casting;

FIG. 6 is a cross-sectional view as in FIG. 4 showing a preferred embodiment of the retaining means, and a crown or its precursor in place on the tooth under repair;

FIG. 7 is an isometric view of the isolated aforesaid one retaining means or component of FIG. 6;

FIG. 8 is an isometric view of a precursor molding form for the aforesaid other retaining means or component;

FIG. 9 is an isometric view of the said other retaining means or component of FIG. 6;

FIG. 10 is an isometric, assembly procedural view of the other retaining component of FIG. 6;

FIG. 12 is an isometric view of a full dental arch embodiment of a mold device in accordance with the present invention;

Figure 11:
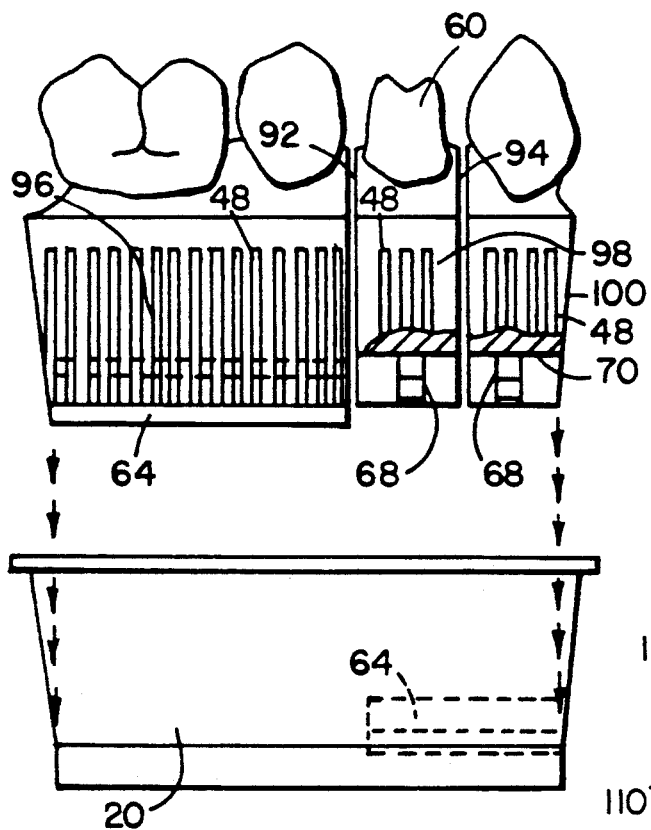
FIG. 11 is a side view, partially in section, of the mold device of FIG. 6 and positive dental casting shown in disassembled form for clarity.
Figure 14:
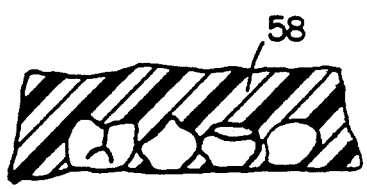
FIG. 14 is a longitudinal cross-sectional view of a typical elastomeric dental negative casting or dental impression.

Referring to teh drawings wherein in the several figures the same or equivalent structural elements are numbered the same, wherein dimensions are not to scale and are not necessarily consistent, and with reference to the claims hereof, the present mold device generally designated 16 comprises associated side wall means 18 and 20, end wall means 22 and 24, and floor means 26, all of which provide base cavity means 28 for containing fluid or set dental stone material 30, cooperating interlocking but separable retaining means, one of said retaining means 32 being carried by or integral with said device, and the other 34 of said retaining means being adapted for fixation to said dental stone material, each said retaining means being cooperatively configured with respect to the other such that in their interlocking position, the set dental stone is firmly held in said device.

Figure 13:
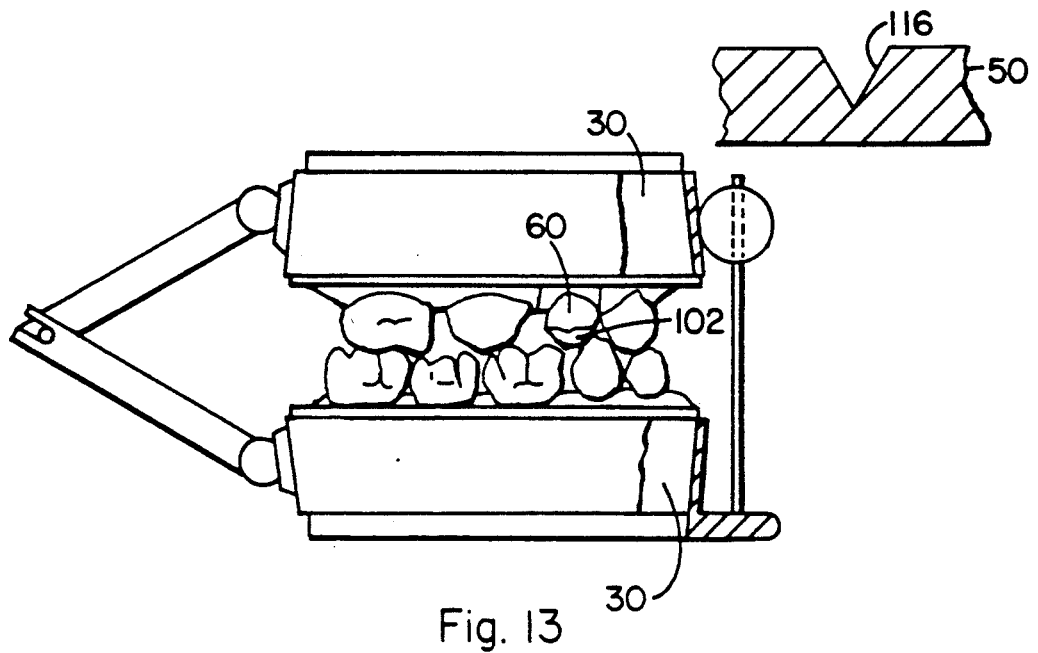
FIG. 13 is a side view, partially in section, of the present mold device and castings mounted in a VERTEX TM articulator for full-bite considerations.

The said one retaining means 32 in its embodiment of FIGS. 1–5 is in the form of a generally longitudinally extending slot 36 in which the said other retaining means or bar 34 is positioned and firmly held by cam surfaces 38 and 40 provided respectively at both ends of the mold and bar. Cam surfaces 38 are provided by the top wall edges of apertures 42, and cam surfaces 40 are provided by the tops of nibs 44 affixed to the ends of bar 34. It is noted that this embodiment of FIGS. 1–5 is mainly useful where the casting does not have to be cut into segments, but where the casting can be utilized in a dental articulator such as shown in FIG. 13.

A plurality of substantially vertical positioning ribs 46 are provided on the inner surfaces of walls 18 and 20 and form complimentary mating ribs 48 in the sides of the casting. These rib sets are especially useful in regard to the embodiments of FIGS. 6–12 and function to properly relocate casting sections within the tray for work-up of the tooth crown or other prosthesis during which several removals and replacements of the sections are often necessary.

The base casting 30 is readily removable from the mold by means of a removal block 50 onto which the mold device can be forced such that the upper surface 52 of the block bears upwardly against the projecting portion 54 of bar 34 to disengage the aforesaid cam surfaces 38 and 40.

Referring to FIG. 4, a typical dental impression of a tooth is shown in dotted outline 56. This impression is formed in an elastomeric chewing gum-like material 58 which may be contained in a suitable mold such as 59, by way of the patient biting down on the material to leave negative impressions therein of the tooth or teeth under repair, as well as other teeth if desired. These impressions are filled with fluid (viscous, flowable) dental stone material to form a positive 60 of the tooth or teeth, the outer surface of this dental stone in the method of the present invention then being brought into contact with the outer surface of the fluid dental stone 30 in the base cavity means 28 to provide a bonding interface such as 62 therebetween for permanently securing the positive 60 to the base 30. The flexible material 58 is then easily stripped from the set positive tooth casting 60.

Referring to FIG. 5, the base 30 with the integrally affixed positive 60 has been pushed upwardly to disengage and separate the retaining means 32, 34, the material 58 also having been removed. The positive tooth 60 can now be worked on to form the desired cap or other prosthesis, and, if desired, can be replaced into the mold device 16 which can be mounted, e.g., by friction fit, into an articulator such as shown in FIG. 13 for adjustment of the cap dimensions to ensure accurate fitting with the proximate teeth and give the proper bite.

In the highly preferred embodiment of the invention shown in FIGS. 6–12, the casting can be cut into two or more segments which can readily be removed and replaced within the mold in their exact initial positions. In this embodiment the said one retaining means which is affixed to the mold device comprises bar 64 cemented at 66 or otherwise attached to floor 26. The said other retaining means 68 of highly resilient plastic or metal material and in clip form is affixed to the base casting 30 by snapping into a specially configured, generally longitudinally extending i.e., generally along longitudinal axis "LA", channel 70 formed in the base casting 30, preferably during its casting. This channel is preferably formed around a retaining component precursor comprising a flexible mold insert 72 which is snapped in place on bar 64 prior to filling cavity 28 with fluid dental stone. Insert 72 is of the same dimensions as clip 68 except that it has a greater flank width W than the flank width W' of said clip, the result of which is to provide gaps 74 and 75 on each side of bar 64 to allow the flanks 76 of the clip to first expand outwardly over the head 78 of bar 64 and then to properly contract thereover. It is noted that the vertically oriented dimensions of bar 64, clip 68, and insert 72 are preferably selected to provide a gap 80 for ensuring bottoming out of the base casting 30 on floor 26 to enhance the seating stability of the base casting within the mold or tray. In this regard the cam surfaces, 38 on bar 64 and 40 on clip 68 are allowed by way of gaps 75 and 80 to essentially fully develop, upon retraction of initially expanded clip flanks 76, the vector forces generally designated 82 which tend to urge the base casting toward floor 26 and maintain the aforesaid seating stability.

As shown in FIG. 10, the clip or clips 68, after removal of insert 72, are readily pushed into their desired positions in channel 70 by means of tool 84 having a head 86 which is dimensioned to bear against the end surface 88 of the clip. The clip may be provided with ridges such as 90 to provide therefor additional resistance to rotation of the clip within the channel.

Referring to FIG. 11, the base casting 30 and attached positive casting 60 are shown as segmented by cutting at 92, 94 into segments or dies 96, 98 and 100. Such segmentation is desireable, e.g., for working up a crown such as 102 shown in FIG. 6 wherein repeated reassemblings into the mold and removals therefrom of the casting are necessary. For such situations where only positive casting 60 is to be worked on, segments 96 and 100 typically need not be further removed from the mold after cuts 92 and 94 have been made and these segments may be cemented as in FIG. 6 at 66 to the floor without removal of the channel maker or insert 72 should, in fact, such an insert be employed at all for such inactive segments. See, for example, Procedure B below. For removing, e.g., die 98 from its associated bar 64 the upper edge of the casting and/or the positive tooth itself may be grasped and pulled upwardly from the tray. Also, a working tray identical in all respects to the molding tray except having a reduced height may be used for operations subsequent to the initial casting such that additional upper areas of the die are available for easy grasping.

The full dental arch mold device of FIG. 12 is provided with the same components as in FIGS. 1–11, but in curved form. It is preferred that this arch embodiment be provided with one or more spaced bridge elements such as 102 integral with both sides of slot 36 in order to provide proper rigidity to the mold. It is noted that the term "longitudinal axis" also applies to this arch shaped mold with respect to the direction of the curved slot 36 and a retaining means extending through or affixed therein.

Following are two alternative exemplary procedures A and B through which the embodiment of FIGS. 6–11 can be utilized.

Procedure A:
1. Insert bar into tray slot;
2. Place rubber channel maker or insert over bar;
3. Mix dental stone and pour tray and impression full;
4. Allow to harden;
5. Place tray onto metal removal block and press down to free model from the tray;
6. Remove the rubber channel maker;
7. Insert the bar back into the tray slot;
8. Place a small bead of glue along the underside of bar;
9. Separate dies (casting segments) with saw cuts;
10. Slide a clip into each die using the seating tool;
11. Dies can now be trimmed, mounted, and replaced accurately into the positioning tray.

Procedure B:
1. Insert bar into tray slot;
2. Cut the rubber channel maker into sections of desired size to fit the area or areas, i.e., dies and snap onto the bar in the desired area or areas;
3. Mix dental stone and pour tray and impression full;
4. Allow to harden;
5. Place tray onto metal removal block and press down to free model from the tray;
6. Separate dies with saw cuts, cutting through the bar at the end of each channel maker;

7. Remove the channel maker sections and the bar within it;
8. Replace this piece of bar into the tray slot and run a small bead of cement on the underside;
9. Slide a clip into each die;
10. Replace, if desired, the non-clip bar segment or segments into the tray slot and cement in place;
11. Die can now be trimmed, mounted, and replaced accurately into the tray.

Figure 15:
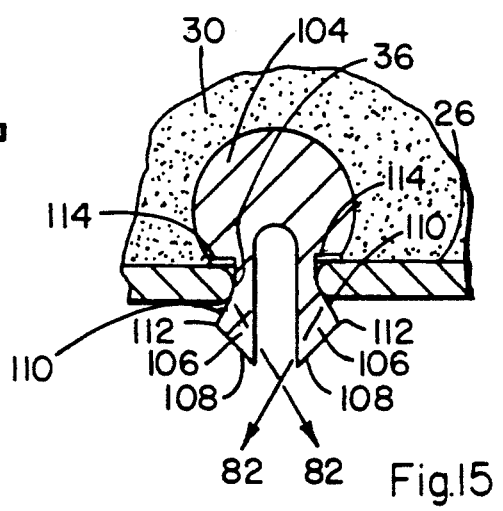
FIG. 15 is an enlarged cross-sectional view similar to FIGS. 4 and 6, but of another preferred embodiment of the retaining means.

Referring to FIG. 15, another preferred embodiment of the retaining means is shown as comprising substantially longitudinally extending slot 36, preferably with slightly rounded edges, and bar 104 which is the equivalent of bar 34 but which, in addition, is provided with a plurality of or a single elongated set of opposed camming prongs 106, each prong being provided with generally linearly opposed force generating cam surfaces 108 and 110. In operation, as the base casting or any segment or die cut therefrom, with bar 104 affixed thereto is pushed downwardly into the mold or tray, the cam surfaces 108 will compress the prongs toward each other and allow crests 112 thereof to pass by the edges of slot 36. This passage then allows the resilient prongs to spring apart and engage cam surfaces 110 thereof with the slot edges with sufficient energy to create vector forces 82 urging the base casting firmly toward floor 26. To maximize this effect it is preferred that for the casting of base 30 onto bar 104, removable spacers such as 114 be provided along the entire length of bar 104 on each side thereof to ensure bottoming out, or at least the tendency to bottom out, of the casting on floor 26 after removal of these spacers from the hardened base casting. For this embodiment the removal block 50 preferably is provided with a groove 116 the sides of which can engage cam surfaces 108 and help to compress the prongs together in cooperation with cam surfaces 110 during removal of the casting from the tray.

This invention has been described in detail with particular reference to preferred embodiments thereof, but it will be understood that variations and modifications will be effected within the spirit and scope of the invention.

I claim:

1. A dental stone casting mold device comprising associated side wall means, end wall means and floor means forming an open top cavity means having a longitudinal axis, said cavity means being adapted for containing set dental stone material, retaining bar means removable affixed to said floor means substantially along said longitudinal axis thereof and extending upwardly from said floor means, said retaining bar means having a generally upright, bulbous cross-sectional configuration providing first cam surface means adapted to provide vector forces directed generally toward said floor means, said retaining bar means being removably receiving on its outer surface portions a cooperating snap interlocking but separable retaining socket type clip means affixed to a hardened dental stone casting, said clip means having second cam surface means oppositely facing to said first cam surface means for engaging said first cam surface means and forcing said clip means and the casting affixed thereto toward said floor means.

2. The mold device of claim 1 wherein at least one of said bar means or clip means is resiliently distortionable by contact with the other, and the potential energy of said vector forces is generated by resilient distortion of said at least one bar means or clip means during forcing thereof toward its interlocking position.

3. The mold device of claim 2 shaped to provide elongated cavity means, and wherein each said bar means and clip means is elongated and oriented substantially longitudinally of said cavity means.

4. The mold device of claim 1 shaped to provide elongated cavity means, and wherein each said bar means and clip means is elongated and oriented substantially longitudinally of said cavity means.

5. The mold device of claim 1, wherein said retaining bar means is provided with a substantially wedge-shaped, cross-sectional configuration on its bottom portion, attachable to said floor means in an interlocking position so as to maintain vector forces on said dental stone material directed generally toward said floor means.

6. The mold device of claim 1 wherein at least one substantially longitudinally extending slot means is provided in said floor means and is adapted to function as a supporting structure for said elongated retaining bar means when inserted therethrough.

7. The mold device of claim 6 wherein said at least one slot means comprises multiple longitudinally spaced slots.

8. The mold device of claim 1 wherein said cavity means has the general configuration selected from the group consisting of a dental arch and a segment of a dental arch.

9. The mold device of claim 1 wherein said retaining clip means is resiliently flexible, has a generally socket shaped cross-sectional configuration, and is provided with lead-in flank portions which are outwardly cammable by said retaining bar means during the interlocking operation to generate the potential energy of said vector forces.

10. The mold device of claim 1 wherein substantially vertically oriented locator ridge means is provided on the inside of said side wall means for aiding in proper reassembly of cast dental stone segments into said mold device.

11. The method for preparing a dental stone positive casting of a tooth in a casting mold device having interconnected side wall means, end wall means and floor means providing base forming elongated, open top cavity means for containing fluid or set dental stone material, comprising the steps of providing on said device one element of a separable, interlocking retaining means, mounting a cooperating other element of said retaining means in removable but frictional interlocking position on said one element within said cavity means, each said element being cooperatively configured with respect to the other such that when they are forced toward an interlocking position, vector forces are created which would tend to urge set dental stone material toward said floor means, filling said cavity means with fluid dental stone, filling a dental impression means with fluid dental stone, bringing the exposed surfaces of the fluid dental stone of the cavity means and impression means into contact to provide a bonding interface therebetween, and allowing said dental stone material to harden and affix said other element of said retaining means thereto for allowing removal of the resultant positive casting from said cavity means with said other element of said retaining means affixed thereto.

* * * * *